United States Patent [19]

Brown et al.

[11] Patent Number: 5,035,468
[45] Date of Patent: Jul. 30, 1991

[54] SURGICAL SCRUB BRUSH

[76] Inventors: James Brown, 690 Bedford Rd., Armonk, N.Y. 10549; Jack W. Kaufman, 357 Frankel Blvd., Merrick, N.Y. 11566

[21] Appl. No.: 522,677

[22] Filed: May 11, 1990

[51] Int. Cl.⁵ .............................................. A46D 3/00
[52] U.S. Cl. ..................................................... 300/21
[58] Field of Search ............... 401/28; 15/114; 300/21

[56] References Cited

U.S. PATENT DOCUMENTS

| | | | |
|---|---|---|---|
| 2,989,767 | 6/1961 | Charvat | 300/21 X |
| 3,447,181 | 6/1969 | Coker et al. | 15/114 X |
| 3,556,667 | 1/1971 | Kaufman | 15/114 |
| 3,641,610 | 2/1972 | Lewis | 15/114 |
| 4,181,446 | 1/1980 | Kaufman | 15/114 X |
| 4,479,277 | 10/1984 | Gilman et al. | 15/114 X |
| 4,936,633 | 6/1990 | Weihrauch | 300/21 |

Primary Examiner—Mark Rosenbaum
Attorney, Agent, or Firm—Lackenbach Siegel Marzullo & Aronson

[57] ABSTRACT

This application discloses a method for assembling a scrub brush having a plurality of bristles integrally on one side of a thermoplastic backing and an open-cell organic sponge bonded to the other side of the backing by carrying out successively the following steps:
 a) forming the thermoplastic brush and bristles;
 b) melting a plurality of protrusions on the side of the backing away from the bristles with applied heat;
 c) placing the sponge on the molten protrusions; and
 d) maintaining contact between the molten protrusions and the sponge;

whereby the molten protrusions are drawn by capillarity into the stroma network of the sponge.

19 Claims, 1 Drawing Sheet

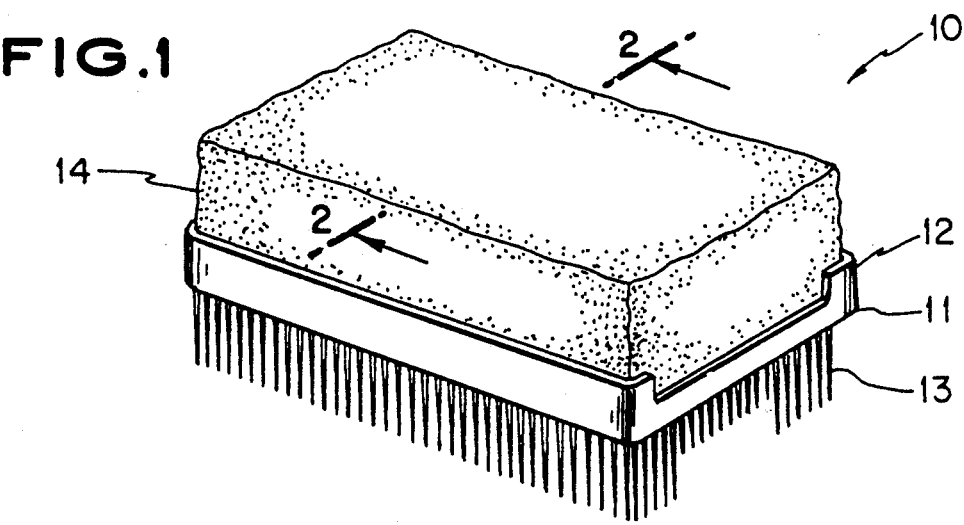
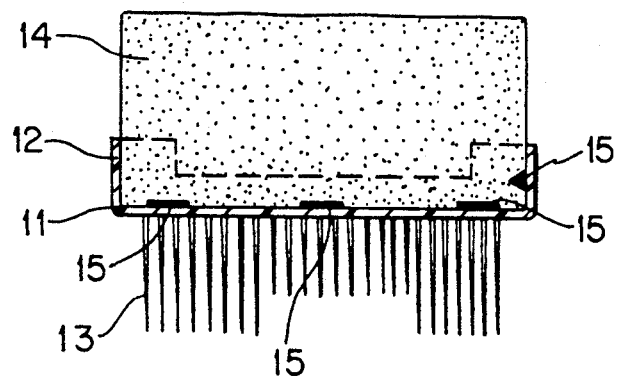
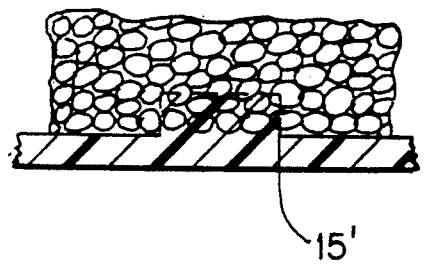
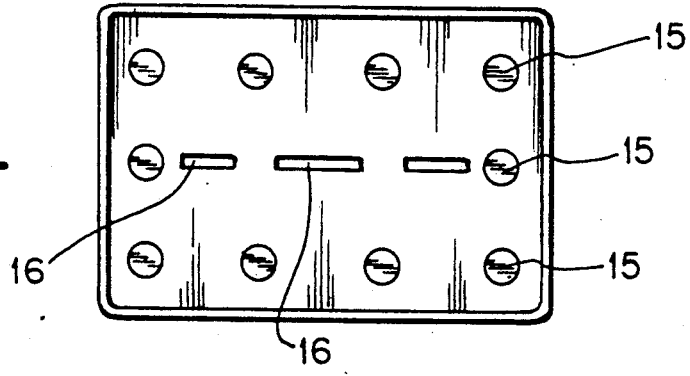
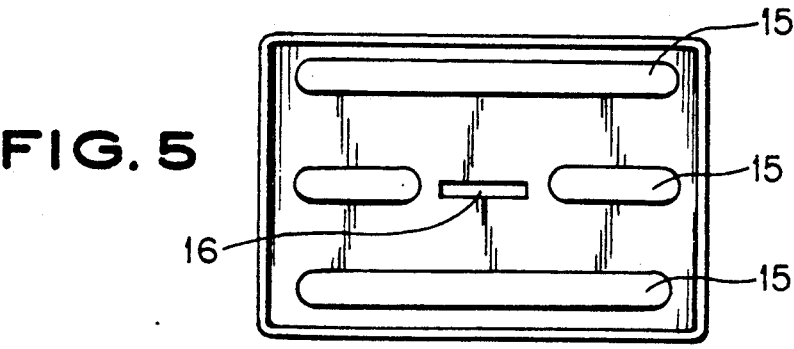

SURGICAL SCRUB BRUSH

FIELD OF THE INVENTION

This invention relates to scrub brushes, more particularly, to resilient surgical scrub brushes. This type of scrub brush has a bristle side made of thermoplastic bristles integral with a hard backing and a spongy, resilient side acting as a reservoir for solutions of disinfectant.

BACKGROUND OF THE INVENTION

U.S. Pat. No. Des. 236,564 shows a combined brush and sponge on opposite sides of a backing. The bristles vary markedly in height.

U.S. Pat. No. Des. 242,668 shows a combined brush and sponge on opposite sides of a backing with reservoirs. The bristles vary somewhat in height.

U.S. Pat. No. 3,447,181 shows uniform bristles integral with a backing holding a sponge on the opposite side. Surgical detergent is placed in the sponge under timed release at different depths.

U.S. Pat. No. 3,556,667 shows opposing bristles and sponge with a flexible wall so that use of the sponge causes dispensing of the cleansing compound.

U.S. Pat. No. 3,704,072 shows opposing bristles and sponge with carrying means in the form of elongated slots to carry the cleaner from a source to the bristles.

U.S. Pat. No. 4,479,277 shows a scrub brush having a housing holding a sponge. The brush has a forward portion with bristles at an acute angle, a movable pick on the housing. The sponge has a lateral slit to receive the top-front edge of the forward portion of the brush.

OBJECTS OF THE INVENTION

It is an object of this invention to provide a scrub brush with a reservoir inert to the oxidative or germicidal cleansing solutions.

It is a further object to provide a firm bond between the brush section and the spongy reservoir section of a scrub brush without the use of adhesives.

Yet another object of the invention is to provide a means for joining the spongy reservoir to the backing of the scrub brush quickly, simply, and at minimum expense.

Yet a further object is to provide a method for assembling a scrub brush with a spongy reservoir employing unskilled workers.

Still another object of the invention in addition to the others is to provide a scrub brush having a spongy reservoir made from a minimum number of easily sterilizable materials.

Other objects will be apparent to those skilled in the art.

SUMMARY OF THE INVENTION

Surprisingly, the objects of the invention enumerated above are met by having an integral hard back brush made of a stable, sterilizable, rather low melting thermoplastic material, creating protrusions on the inside of the hardback away from the integral bristles, melting the thermoplastic protrusions, and maintaining contact between the molten protrusions and the stable, spongy reservoir, whereby the molten protrusions flow into the stroma network of the sponge forming a strong, stable bond without adhesives.

BRIEF DESCRIPTION OF THE FIGURES

FIG. 1 is a perspective view of the surgical scrub brush of the invention showing an integral hard back brush with circumferential flanges for holding the spongy reservoir.

FIG. 2 is a cross-sectional view taken along the line 2—2 in FIG. 1 showing the arrangement of the hard back brush, integral bristles of the brush, flanges, and spongy reservoir.

FIG. 3 is an enlarged detailed view of a portion of FIG. 2 showing how a molten protrusion from the thermoplastic hardback has flowed into the foraminous sponge.

FIG. 4 is a top plan view of the thermoplastic hard back showing one possible arrangement of thermoplastic protrusions, not to scale, and a slit to the brush from the spongy reservoir, not yet in place.

FIG. 5 is a top plan view showing alternative linear protrusions, not to scale, and a slit to the brush from the spongy reservoir, not yet in place.

DETAILED DESCRIPTION OF THE PREFERRED EMBODIMENTS

Generally, the present invention comprises melting a plurality of protrusions on the side of a thermoplastic hard back scrub brush away from the integral bristles, placing an organic sponge on the molten protrusions, and maintaining contact between the molten protrusions and the sponge long enough for the thermoplastic polymer to flow into the sponge. Because no adhesives are employed, the germicide solution is stronger than it would be if the antiseptic were to react with adhesives.

FIG. 1 shows a surgical scrub brush 10 having a thermoplastic hard back 11, flanges 12, and integral bristles 13. The flanges can be of any relative size and shape and extent compared to the backing. One or more sides can be without flanges. The bristles are preferably made by injection molding integral with the backing, as are the flanges, but this is not necessary. The bristles can be of the same size or of different lengths, as shown in FIGS. 1 and 2. Flanges are preferred, but not necessary.

The backing 11, although shown as rectilinear in FIG. 1 can be any shape or relative dimension. Also, the spongy reservoir 14 is preferably rectilinear, but also may have any desired shape or relative dimensions.

The thermoplastic brush or hardback may be molded from any conventional thermoplastic resin such as polyethylene, polypropylene, nylon, polystyrene, polymethylstyrene and the like. Injection molding of integral backing, bristles, and flanges is preferred, but other conventional forming processes for thermoplastic resins may also be employed.

Spongy reservoir 14 may be any natural or synthetic organic polymeric sponge exemplified but not limited by polyurethane, polyurethane, ether, cellulose, nylon, silicone rubber, polyethylene, homopolymer or copolymeric polyether, synthetic or natural rubbers. It is preferably resilient.

Thermoplastic protrusions 15 in the Figures are preferably molded into the hard back 11, but also may be spikes molded into the flanges 12, as shown on the right side of FIG. 2. These protrusions may be small spherical ones, as in FIG. 4 or linear ones, as in FIG. 5, or any convenient shape. They may be in regular or random array. Preferably, they have a base approximately 5 mm in diameter and are approximately 3 mm high. Preferably, there is one meltable protrusion for each 5 sq. cm of the area of the backing, but this ratio can vary from about one protrusion per sq. cm to one per 50 sq. cm.

Openings 16 are preferably slits, as shown in FIGS. 4 and 5, but may be of any convenient shape. Their purpose is to allow the soap, germicide, fungicide, disinfectant, sterilant, or cleansing agent held in the spongy reservoir to flow into the brush, when pressure is applied to the sponge.

The germicides, disinfectants, soaps, cleansing agents, bacteriacides, antiseptics, fungicides, sporicides, or sterilants employed for pre-surgical, during surgical, or post-surgical procedures may be one or more of mixtures of various types of compounds. Among these types of compounds are oxidizing agent, iodine or iodine complexes or carriers, quaternary nitrogen compounds, aldehydes, halogenated hydrocarbons, non-ionic surface active agents, carboxylic soaps, and any other conventional germicidal agents. More specifically, solutions of permangnate, solutions of hypochlorite, iodophores such as providone, hexachlorophene, glutaraldehyde, trimethylbenzylammonium chloride, phenols, conventional soaps, conventional ethoxylated nonyl alcohol detergents, exthoxylated polypropylene detergents, and the like are suitable for the present invention. The germicidal compound is conventional and not the essence of the novel surgical scrub brush of the present invention.

In order to melt protrusions 15, so the molten material may flow into the foraminous stroma network 15, of the spongy reservoir, as shown in FIG. 3, any conventional heating system may be employed. Electric resistance heating of the pre-formed, thermoplastic protrusions 15, preferably by platens without touching them, creates a regular or random set of molten drops on the backing 11 without deforming scrub bristles 13. Hot air heating, steam heating, hot liquid transfer heating, ultrasound heating, or even the friction of incipient plastic welding from a matching set of rotating exogenous small members could also be employed. Electric heating is preferred. The heating time varies from about 0.1 sec to about 5 secs; preferably about 0.5 sec. Depending on the thermoplastic employed, the temperature of the melt varies from about 60 degrees C to about 250 degrees C.

After the short heating time of the array of thermoplastic small protrusions 15, the molten array is allowed to be in contact with the properly aligned spongy reservoir member. Preferably, the heating should not be continued during this brief time of contact to avoid burning the open-cell foam. This contacting time can range from about 0.2 sec to about 5 sec to allow the molten thermoplastic to wick into the foraminous stroma network to form the bond 15'. Because both the molten protrusion and the open-cell foam are of organic composition, the melt should wick by capillarity into the stroma network of the sponge with low contact angle. Preferably, this occurs in less than one second, so that the process may be easily automated. Any pressure exerted by the foam on the molten protrusions should be minimal to nil. Mere brief contact without pressure is preferred, in order not to distort the array of molten protrusions or spikes 15. Also, any pressure should be minimal so that the integral bristles 13 are not distorted in shape.

As disclosed in U.S. Pat. No. 3,556,667, the assembled spongy-reservoir/thermoplastic unit may be furnished in a compressed condition, may additionally comprise a protective covering, may be impregnated with steriliz-ing agent with or without freeze-drying, or may be encapsulated for storage and transport.

As shown in FIG. 2, the bristles may be uniform or varied.

The reservoir elements or openings 16 may be open-ended or sealed to break under finger pressure. They may be constructed and arranged to direct the flow of germicidal compound directly onto the area to be scrubbed or merely generally to the bristles 13. This invention may be substantially identical without any apertures, slits, or orifices 16.

While this invention has been shown, described, and illustrated in terms of preferred embodiments and parameters, the scope of this invention is not so limited. Modifications may be made and still fall within the scope and breadth of the claims below for which Letters Patent are sought.

We claim:

1. A method for assembling a scrub brush having a plurality of bristles integrally on one side of a thermoplastic backing and an open-cell organic sponge bonded to the other side of the thermoplastic backing comprising the steps of:
   a) forming a thermoplastic brush with integral bristles oriented primarily perpendicular to a backing;
   b) melting a plurality of protrusions on the side of the backing away from the bristles by heating the protrusions from about 0.1 to about 5 seconds;
   c) placing the sponge on the molten protrusions with minimal pressure; and
   d) maintaining contact between the molten protrusions and the sponge without heating; whereby the molten protrusions migrate by capillarity sufficiently into the stroma network of the sponge to form a firm assembly without the use of adhesives.

2. The method of claim 1, wherein the thermoplastic backing is selected from the group consisting of polyethylene, polypropylene, polystyrene, polymethyl methacrylate, a nylon, a polyacetal, polyvinyl chloride, ethyl cellulose, and mixtures and copolymers thereof.

3. The method of claim 2, wherein the thermoplastic backing is of polyethylene.

4. The method of claim 3, wherein the open-cell, organic sponge is polyurethane ether.

5. The method of claim 1, wherein the open-cell, organic sponge is selected from the group consisting of polyurethane ether, cellulose, polyether, nylon, silicone rubber, polyethylene, synthetic rubber, natural rubber, and mixtures and copolymers thereof.

6. The method of claim 1, wherein the melting of step b takes place in less than one second.

7. The method of claim 1, wherein the open-cell, organic sponge is resilient.

8. The method of claim 1, wherein the thermoplastic backing has side flanges partially covering the side of the sponge.

9. The method of claim 8, wherein the side flanges also have meltable protrusions.

10. The method of claim 9, wherein the meltable protrusions from the side flanges are in the form of small spikes.

11. The method of claim 1, wherein the backing has a plurality of reservoirs for holding liquid antiseptic.

12. The method of claim 1, wherein the melting of step b is accomplished by a heating means selected from the group consisting of electrically heated platen dies, ultrasonic heating, hot air heating, steam heating, and hot liquid transfer heating.

13. The method of claim 11, wherein the heating means is by electrically heated platen die.

14. The method of claim 1, wherein the assembly process takes less than five seconds.

15. The method of claim 1, wherein the assembly process takes less than three seconds.

16. The method of claim 1, wherein the meltable protrusions are in a regular array.

17. The method of claim 1, wherein the meltable protrusions are randomly spaced.

18. The method of claim 1, wherein the meltable protrusions have a base of approximately 5 mm in diameter and are approximately 3 mm high.

19. The method of claim 1, wherein there is one meltable protrusion approximately for each 5 sq. cm of area of the backing.

* * * * *